US005686061A

United States Patent [19]
Li et al.

[11] Patent Number: 5,686,061
[45] Date of Patent: Nov. 11, 1997

[54] PARTICULATE CONTRAST MEDIA DERIVED FROM NON-IONIC WATER SOLUBLE CONTRAST AGENTS FOR CT ENHANCEMENT OF HEPATIC TUMORS

[75] Inventors: Chun Li; Sidney Wallace; Zuxing Kan, all of Houston; David J. Yang; Li-Ren Kuang, both of Sugar Land, all of Tex.

[73] Assignee: The Board of Regents of the University of Texas System, Austin, Tex.

[21] Appl. No.: 225,665

[22] Filed: Apr. 11, 1994

[51] Int. Cl.$^6$ ..................................................... A61K 9/16
[52] U.S. Cl. .................. 424/9.454; 424/9.45; 424/9.451; 424/9.452; 424/9.453; 549/229
[58] Field of Search .......................... 424/9, 9.45, 9.451, 424/9.452, 9.453, 9.454, 9.455; 549/229

[56] References Cited

U.S. PATENT DOCUMENTS

| | | | |
|---|---|---|---|
| 4,716,225 | 12/1987 | Ledley et al. | 536/122 |
| 4,873,075 | 10/1989 | Counsell et al. | 424/1.1 |
| 4,957,729 | 9/1990 | Counsell et al. | 424/5 |
| 5,093,042 | 3/1992 | Counsell et al. | 260/408 |

FOREIGN PATENT DOCUMENTS

| | | |
|---|---|---|
| 0 083 964 | 7/1983 | European Pat. Off. . |
| 0 133 248 | 2/1985 | European Pat. Off. . |
| 0 431 838 A1 | 6/1991 | European Pat. Off. . |
| 5208921 | 8/1993 | Japan . |
| WO 90/07491 | 7/1990 | WIPO . |
| WO 94/14478 | 7/1994 | WIPO . |

OTHER PUBLICATIONS

Newton, "Structure–Toxicity Relationships of Iodinated Aromatic Carbonates and Related Compounds," Jnl of Pharmaceutical Sciences, vol. 67, No. 8 (Aug. 1978).

Newton, "Iodine–Containing Organic Carbonates as Investigative Radiopaque Compounds," Jnl of Medicinal Chem., vol. 19, No. 12 (Dec. 1976).

Pillai, et al., "Heterocyclic Nonionic X–ray Contrast Agents. 3. The Synthesis of 5-[4-(Hydroxymethyl)-2-oxo-3-oxazolidinyl]-2,4,6-triiodo-1,3-benzene-dicarboxamide Derivatives," Jnl. Org. Chem. 59, pp. 1344-1350 (Mar. 1994).

Ranganathan, et al., "The Chemical, Biological, and Physical Properties of 5–Heterocycle Substituted 2,4,6–Triiodo–1,3–Benzenedicarboxamide Derivatives," Investigative Radiology, vol. 26, Supp. No. 1 (Nov. 1991).

Morris, "Inotropic Effects of Sodium Citrate in a Nonionic Contrast Medium," Jnl of Clinical and Laboratory Investigative Radiology, vol. 25, Supp. (Sep. 1990).

Li, et al., "Preparation, Characterization, and Evaluation of Ioxilan Carbonate Particles for Computed Tomography Contrast Enhancement of Liver," Jnl of Clinical and Laboratory Investigative Radiology, vol. 29, No. 11 (Nov. 1994).

Sands et al., "Computed Tomographic Enhancement of Liver and Spleen in the Dog with Iodipamide Ethyl Ester Particulate Suspensions," pp. 408–416 (Jun. 1987).

Violante et al., "Maximizing Hepatic Contrast Enhancement With A Particulate Contrast Agent in Computed Tomography," pp. 69–75 (Mar. 1981).

Masazumi Ishikawa, et al., *Fundamental Study of Positive Contrast Media of Hepatic CT by Micro–Barium Sulphate Particles*, 1478–1488 (Nov. 1987).

M.R. Violante, et al., Biodistribution of a Particulate Hepatolienographic CT Contrast Agent; A Study of Iodipamide Ethyl Ester in the Rat, Investigative Radiology, vol. 16, Jan. 1981, 40–45.

Michael R. Violante, et al., Particulate Contrast Media for Computed Tomographic Scanning of the Liver, Investigative Radiology, vol. 15, Nov. 1980, S171–S175.

M. Sovak, et al., Current Contrast Media and Ioxilan Comparative Evaluation of Vascular Pain by Aversion Conditioning, Investigative Radiology, vol. 23, Sep. 1988, S84–S87.

Steven E. Seltzer, et al., Liposomes Carrying Diatrizoate Characterization of Biophysical Properties and Imaging Applications, Investigative Radiology, Mar. 1984, 142–151.

David J. Yang, et al., *Evaluation of Poly(dl–latide) Encapsulated Radiopaque Microcapsules*, American Chemical Society, 371–381 (Apr. 1993).

Peter R. Mueller, et al., Medical Progress: Interventional Radiology in the Chest and Abdomen, The New England Journal of Medicine, May 1990, 1364–1374.

I. Kofi Adzamli, et al., Production and Charaterization of Improved Liposomes Containing Radiographic Contrast Media, Investigative Radiology, Nov. 1990, 1217–1223.

Paul H. Sugarbaker, et al., Improved Detection of Focal Lesions with Computerized Tomography Examination of the Liver Using Ethiodized Oil Emulsion (EOE–13) Liver Contrast, Cancer, Oct. 1984, 1489–1495.

Errol Lewis, et al., CT Detection of Hepatic Metastases with Ethiodized Oil Emulsion 13, Journal of Computer Assisted Tomography, Dec. 1982, 1108–1114.

*Primary Examiner*—Brian M. Burn
*Attorney, Agent, or Firm*—Rosenblatt & Redano, P.C.

[57] ABSTRACT

The present invention provides a method for chemically modifying non-ionic, water soluble particulate contrast agents so that they degrade in vivo to their non-ionic parent contrast material and carbon dioxide. According to the present invention, known particulate, non-ionic contrast agents are chemically modified to form a precursor or "prodrug" comprising cyclic carbonates and carbamates of the parent compound. The resulting cyclic carbonates and carbamates are lipid soluble, biodegradable, and can be prepared in large quantities using well-established methods. These cyclic carbonates and carbamates can be converted to particulate contrast media using simple, well known techniques, such as solvent-extraction or solvent evaporation.

16 Claims, 7 Drawing Sheets

Number-Weighted Gaussian Analysis (Solid Particles)

IX-c 5-3-93, L.1  (C370.TBL 5/3/93)

| Diam. nanometers | Numbers Rel. |
|---|---|
| 229.1 | 0.000 |
| 264.5 | 0.000 |
| 305.5 | 0.000 |
| 352.7 | 0.000 |
| 407.3 | 0.001 |
| 470.4 | 0.004 |
| 543.2 | 0.023 |
| 627.3 | 0.093 |
| 724.3 | 0.271 |
| 836.5 | 0.575 |
| 965.9 | 0.889 |
| 1115.4 | 1.000 |
| 1288.1 | 0.818 |
| 1487.5 | 0.487 |
| 1717.7 | 0.211 |
| 1983.6 | 0.066 |
| 2290.6 | 0.015 |
| 2645.1 | 0.003 |
| 3054.5 | 0.000 |
| 3527.3 | 0.000 |
| 4073.3 | 0.000 |
| 4703.8 | 0.000 |

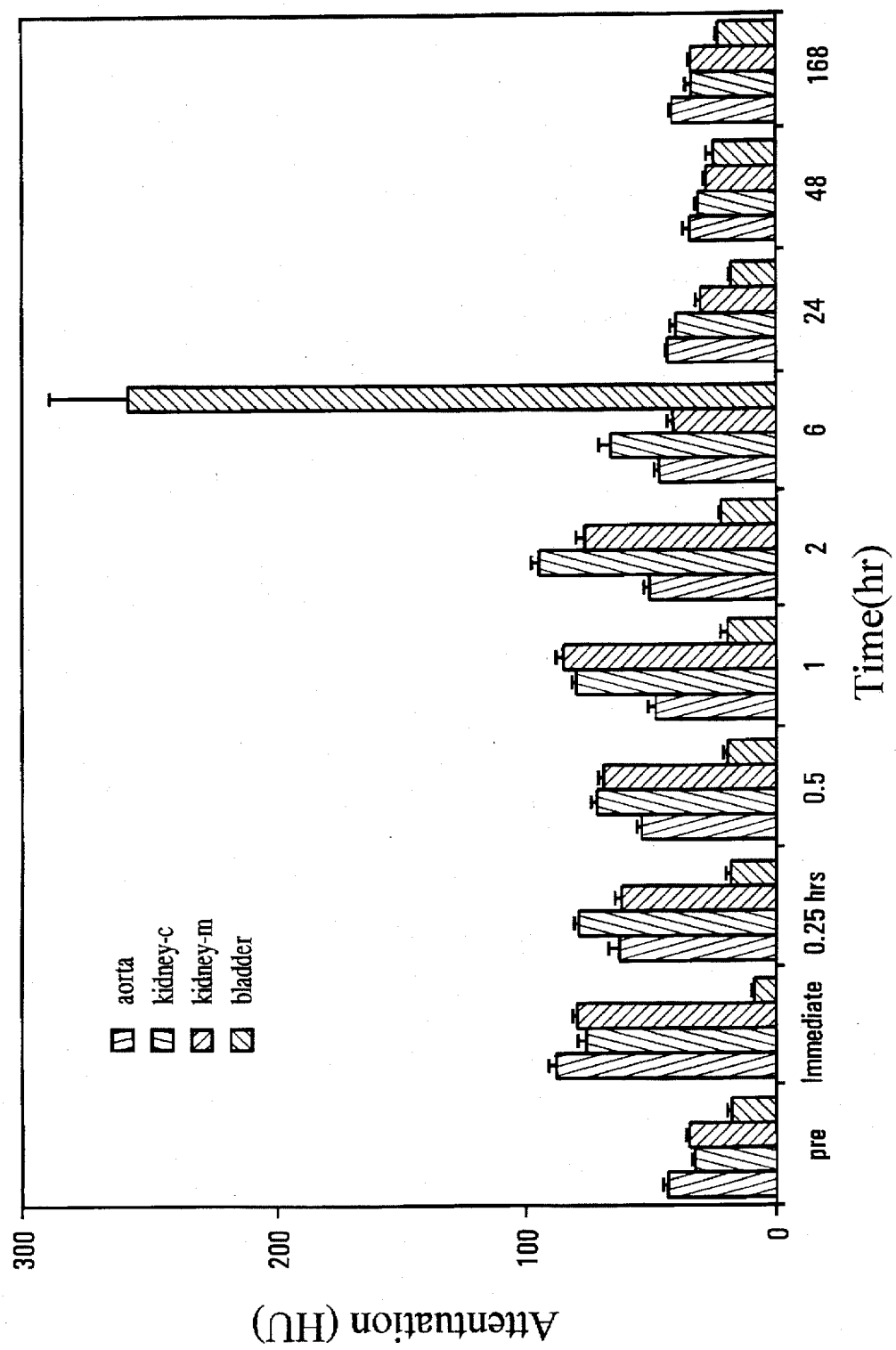

PARTICULATE CONTRAST MEDIA DERIVED FROM NON-IONIC WATER SOLUBLE CONTRAST AGENTS FOR CT ENHANCEMENT OF HEPATIC TUMORS

FIELD OF THE INVENTION

The present invention relates to contrast media used to detect hepatic lesions, and more particularly to non-ionic, particulate contrast media having particles that are not water soluble, but which will degrade to their parent, water soluble, non-ionic contrast agent and carbon dioxide.

BACKGROUND OF THE INVENTION

Assessment of the liver for metastases is important in staging a wide variety of malignancies. Surgical removal of hepatic lesions requires precise diagnosis of the number, size, and location of the tumor(s). Typically, hepatic lesions are diagnosed using computed tomography scanning (CT), or computed tomographic portography (CT angioportography). CT angioportography is performed after the superior mesenteric or splenic artery has been selectively catheterized and injected with contrast media (CM) to opacify the hepatic parenchyma. During CT angioportography lesions in the liver appear as defects in the enhanced parenchyma. Unfortunately, benign and malignant masses can't be differentiated, and the time available for optimal imaging is limited.

CT detection of hepatic lesions generally can be improved using rapid intravenous injection of water-soluble contrast agents combined with fast, incremental CT scanning (bolus dynamic CT). Bolus dynamic CT has an accuracy between about 73%–75% in identifying patients with hepatic metastases (Freeny PC, Marks WM, Ryan JA, Bolen JW. Colorectal carcinoma evaluation with CT. Preoperative staging and detection of postoperative recurrence. Radiology 1986;158:347–353). Furthermore, currently available water-soluble contrast agents produce contrast enhancement for a duration of only minutes before CT densities return to baseline levels.

Particulate contrast agents are a promising avenue for selectively opacifying the liver and for prolonging the radiocontrast effect of the contrast media. Phagocytic cells of the reticulo-endothelial system (RES), the Kupffer cells (KC) of the liver, very efficiently remove foreign particles from the blood. A large proportion of small particles (<5 μm in size) will be removed by the RES within a few minutes. Furthermore, most neoplastic lesions do not contain macrophages. Therefore, targeting the liver with particulate contrast media enhances the liver parenchyma, causing tumors to appear as defects.

Several experimental particulate contrast agents have been developed during the last few decades. These roughly can be divided into three categories: (1) iodinated lipid (EOE-13); (2) radiopaque liposomes; and, (3) particles derived from water-soluble ionic contrast media (iodipamide ethyl ester, or "IDE"). Unfortunately, each of these particulate media has drawbacks.

EOE-13 is a lipid soluble contrast agent which can be formulated as an oil emulsion for intravenous injection. The drawback of EOE-13 is that EOE-13 is not biodegradable. Liposome-based contrast agents have the drawback that they usually have a short shelf-life and the efficiency of encapsulation is low. Although iodipamide ethylester (IDE) particles appeared promising, one of the degradation products of IDE particles in vivo is iodipamide. Iodipamide is ionic and therefore is toxic to endothelial cells, perhaps due to the high osmolarity resulting when it is present. A by-product of the degradation of other similar radiopaque esterified particles also should be the original ionic form of the radiopaque compound.

The osmolarity of body fluids and cell contents must be maintained within a narrow physiological range. The particles present in particulate contrast media are targeted to, and should be degraded by Kupffer cells. Therefore, the osmotic influence of the degradation by-products of these contrast media, particularly if the by-products are ionic, is of major concern. A particulate contrast agent which was biodegradable and produces non-ionic, non-toxic by-products would be highly desirable.

SUMMARY OF THE INVENTION

The present invention provides a method for chemically modifying non-ionic, water soluble particulate contrast agents so that they degrade in vivo to their non-ionic, water soluble parent compound and carbon dioxide. According to the present invention, known particulate, non-ionic contrast agents are chemically modified to form a precursor or "prodrug" comprising cyclic carbonates and carbamates of the parent compound. The resulting cyclic carbonates and carbamates are lipid soluble, biodegradable, and can be prepared in large quantities using well-established methods. These cyclic carbonates and carbamates can be converted into particulate contrast media using simple, well known techniques, such as solvent-extraction or solvent evaporation.

DETAILED DESCRIPTION OF THE DRAWINGS

FIG. 7 is a plot of the CT pharmacokinetics of aorta, kidney (cortex and medulla), and bladder following injection of 200 mg I/kg body weight of IX-C particles (1–2 μm) presented as a histogram.

DETAILED DESCRIPTION OF THE INVENTION

Figures 1, 2:
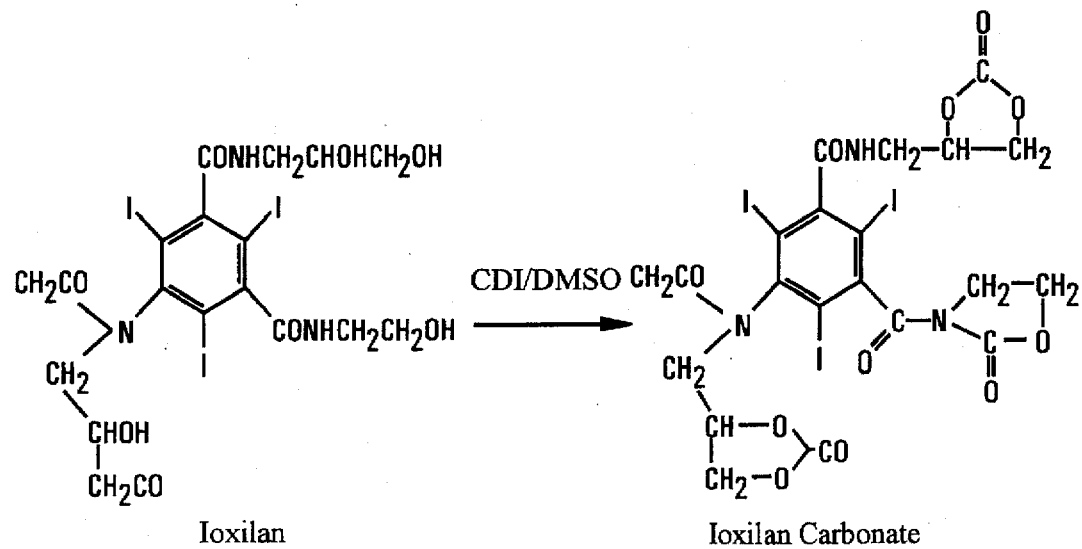
FIG. 1 is a diagrammatic representation of the scheme and the structure of the cyclic carbonate of IOXILAN obtained by reacting IOXILAN with CDI (Carbonyldiimidazole). This synthesis can be used to prepare other non-ionic particulate contrast agents, as well.
FIG. 2 represents the IX-C microparticles' (1–2 μm) size distribution when prepared according to the solvent extraction/evaporation process of the present invention.

The invention is described with reference to a third-generation non-ionic, water soluble contrast agent called IOXILAN. Toxicological and pharmacological studies of IOXILAN indicate that the body has a high overall biological tolerance for IOXILAN. However, other water soluble non-ionic contrast agents, including but not limited to IOHEXOL, IOPROMIDE, IOTROLAN, IOPAMIDOL, METRIZAMIDE, IOGLUNIDE, IOGULAMIDE, and similar agents, also are suitable for use according to the present invention.

Generally, water soluble non-ionic contrast agents suitable for use in the present invention are aromatic compounds substituted with an amount of a radiopaque element sufficient to render the compound detectable by standard diagnostic tools, such as computed tomography. Even a single radiopaque substituent may be sufficient for purposes of the present invention; however, the presence of two or more radiopaque substituents renders the material more detectable. Therefore, it is preferred to have as many radiopaque substituents on the aromatic ring as possible, preferably three such agents on alternating carbons of the aromatic ring. The radiopaque element can be any suitable non-toxic element; however, the preferred radiopaque element is iodine.

The aromatic compound also has at least one amide substituent with an aliphatic vicinal diol and/or 1,3-diol substituent bound to either the carbon or nitrogen of the amide moeity. This hydrophilic aliphatic polyol substituent renders the contrast agent water soluble. In other words, a preferred embodiment of the invention comprises an aromatic ring alternately substituted at the ring carbons with a radiopaque element, preferably iodine, and an aliphatic amide group. Each of the aliphatic amide groups preferably contains at least one hydroxyl group, and at least one of the amide groups must contain a vicinal diol or a 1,3-diol.

The following is an illustration of the general structure of suitable water soluble non-ionic contrast agents:

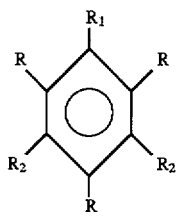

R is a radiopaque element; $R_1$ is an amide group bonded to said aromatic ring at either the nitrogen or the carbon of the amide, the unbonded nitrogen or carbon having a substituent selected from the group consisting of an aliphatic vicinal diol and an aliphatic 1,3-diol; and $R_2$ is selected from the group consisting of a radiopaque element, a hydrogen, an alkyl group having between about 1–4 carbon atoms, and an amide group bonded to the aromatic carbon at either the nitrogen or the carbon of the amide, the unbonded nitrogen or carbon having a substituent selected from the group consisting of hydrogen, an alkyl group having between about 1–3 carbon atoms, and a hydroxylated aliphatic side chain having between about 1–8 carbon atoms. Preferably, the aromatic carbon is substituted with at least two amide groups having a vicinal diol or 1,3-diol substituent and at least two radiopaque elements, preferably iodine.

The foregoing non-ionic contrast agents may be chemically modified to form cyclic carbonates and carbamates. One such suitable method is described in Kutney, J. P., and Ratcliffe A. H. "A novel and mild procedure for preparation of cyclic carbonates. An excellent protecting group for vicinal diols." *Synth. Commun.* 1975;5;47–52 (incorporated herein by reference).

Generally the radiopaque contrast agent is thoroughly mixed with (a) an activating and/or coupling agent, such as carbonyldiimidazole (CDI), a phosgene, a triphosgene, trichloromethyl chloroformate, or other activating/coupling agents known in the art, in (b) a polar aprotic solvent, such as dry dimethyl sulfoxide (DMSO), dimethylformamide, 1-methyl-2-pyrrolidinone, or other polar aprotic solvents known in the art, in the presence of (c) a catalyst capable of catalyzing the formation of cyclic carbonates and carbamates from said water soluble non-ionic CM. Suitable catalysts include salts of alkyl oxides, such as sodium methoxide, sodium ethoxide, potassium methoxide or similar salts. The mixing process typically requires about 30 minutes. After mixing, the solution should be stirred for a time and at a temperature sufficient to permit the formation of cyclic carbonates and carbamates. Typically, the solution should be stirred between about 2–20 hours, preferably at least about 10 hours, at a temperature between about 40°–90° C., preferably at about 70° C.

The reaction then may be terminated by adding an organic solvent, such as methylene chloride, and washing with cold water. The solution should separate into an organic and a water phase, the cyclic carbonates and carbamates remaining in the organic phase, and the DMSO remaining in the water phase. Once the organic phase has been separated, the organic solvent is dried over dehydrating agents, such as $MgSO_4$, $Na_2SO_4$, or a similar agent. The solvent then is filtered and evaporated to dryness so that the product may be collected for further use. FIG. 1 is a diagrammatic representation illustrating the reaction of IOXILAN to form IOXILAN Carbonate according to the present invention.

The following is a general formula which, without limiting the present invention, is believed to represent biodegradable contrast prodrug made from water-soluble non-ionic CM prepared according to the method of the present invention:

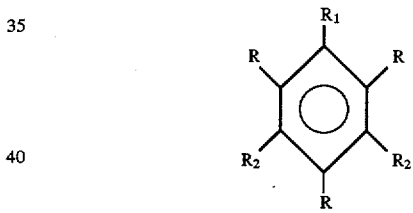

In the foregoing structure, R is a radiopaque element. Preferably all three R groups are radiopaque elements, preferably iodine. $R_1$ is an amide group bonded to the aromatic ring at either the nitrogen or the carbon of the amide moiety, and the unbonded nitrogen or carbon of the amide moiety is substituted by an aliphatic group which includes a cyclic carbonate and/or a carbamate. $R_2$ preferably is another amide group which contains another cyclic carbonate and/or a carbamate; however, $R_2$ also may be a radiopaque element, hydrogen, an alkyl group having between about 1–4 carbon atoms, or any other substituent which will not interfere with the function of the contrast agent—that is, to opacify the liver parenchyma while biodegrading to water soluble, non-ionic by-products.

The prodrugs or precursors of the invention are formulated as injectable microparticles (mean diameter about 1–2 micron) in the following manner. The cyclic carbonate and carbamate derived from the water soluble non-ionic contrast agent(s) is dissolved in organic solvent or solvent mixture, which may include but is not limited to acetone, chlorinated carbon, tetrahydrofuran, dimethylformamide, etc., preferably a mixture of acetone and methylene chloride. The organic solution containing the prodrug is added to an aqueous solution containing an emulsifier, such as polyvinyl alcohol, Tween 80, cellulose, polyvinylpyrrolidone. A preferred emulsifier is polyvinyl alcohol. The mixture then is emulsified mechanically with or without sonication for up to about 10 minutes, and stirred for about another 4 hrs to ensure complete removal of organic solvent. The resulting microparticles are collected following repeated centrifugation and washing steps.

The invention will be more clearly understood with reference to the following examples.

EXAMPLES

Materials

For purposes of the following examples, IOXILAN was supplied by Cook Imaging Corp. (Bloomington, Ind.). Carbonyldiimidazole (CDI), dimethyl sulfoxide (DMSO), magnesium sulfate, methylene chloride, and sodium methoxide were obtained from Aldrich Chemical Co. (Milwaukee, Wis.). Poly(vinyl alcohol) (PVA, MW 30 to 70K) was purchased from Sigma Chemicals Co. (St. Louis, Mo.).

Synthesis of IOXILAN Carbonate

The cyclic carbonate of IOXILAN (IX-C) was prepared using the method of Kutney and Ratcliffe, *Synth. Commun.* 1975; 5; 47–52, incorporated herein by reference. A solution of CDI (4 g, 24 mM) in dry DMSO (15 mL) was dropped into a solution of IOXILAN (4 g, 2.5 mM) in DMSO (10 mL) over a period of 30 minutes and stirred at 70° C. overnight. A catalytic amount of sodium methoxide was added to facilitate the formation of cyclic carbonates. To terminate the reaction, the DMSO solution was diluted with methylene chloride and washed with cold water. The methylene chloride layer was dried over $MgSO_4$ and evaporated to dryness to yield 2.2 g product (yield 50%). TLC (Silica, chloroform:methanol, 10:1) indicated only one spot (Rf= 0.75). IR (KBr, cyclic carbonate): 1780 $cm^{-1}$. Mass spectrum was determined by Fast Atom Bombardment (Kratos MS50, England) using nitrobenzyl alcohol as matrix material: $MH^+$=870. Elemental analysis, calculated C:29.0%, H:2.07%, N:4.83%, I:43.8%; found C:30.6%, H:2.47%, N:4.63%, I:42.0%. Carbon-13 NMR (DMSO-d6) revealed the presence of acetyl methyl carbon (22.3 ppm), aliphatic carbons (40.7 to 74.9 ppm, 8C), aromatic carbons (91.0, 99.5, 100.4, 146.7, 151.0, and 151.9 ppm), and amide carbonyl carbons (167.3 to 170.2 ppm, 3C), representing the basic structure of IOXILAN. Cyclic carbonate carbons and carbamate carbon (148.6, 154.2, 154.5) were also present.

Preparation of IX-C Particles

IX-C particles were prepared by a solvent extraction/ evaporation method. A solution of IX-C (3.0 g) in acetone (20 mL) and methylene chloride (60 mL) was added to an aqueous solution of PVA (400 ml, 1%, w/v). The mixture was emulsified with an emulsifier (Tekman, Germany) for 1 minute and then stirred at 400 rpm for 4 hours to ensure complete removal of organic solvent. The resulting emulsion was centrifuged at 3000 rpm, resuspended in distilled water, filtered through a nylon filter (5-μm pore size), and centrifuged again. The process was repeated three times. Finally, the centrifuged product was resuspended in saline and adjusted to proper volume for in vitro and in vivo testing.

Physical Characterization of IX-C Particles

Surface characteristics of the particles were evaluated with a scanning electron microscope (Hitachi Model S520). For sample preparation, microspheres were placed onto a 0.1-μm Nuclepore membrane, mounted onto stubs and sputter-coated with 200Å gold-palladium (80:20) in a Hummer VI (Technics, Springfield, Va.). The size distribution of IX-C particles was measured by light scattering with a Nicomp 370 Submicron Particle Sizer (Nicomp Instruments Corp., Goleta, Calif.).

Suspension Stability

Suspension stability of radiopaque particles were observed under light microscopy 20×2.5, Zeiss, Germany) and recorded with a video camera. IX-C particle suspensions in saline and in saline solution of Tween 80 (0.1%, w/w) were studied. After 5 minutes of observation, fresh rat plasma was added onto the suspensions, and the mixtures were observed for an additional 5 minutes to record any changes.

Hydrolyric and Enzymatic Degradation of IX-C Particles

Degradation of IX-C particles was investigated by incubating a suspension of the particles (25 mg) in the following solutions (each 1 ml) at 37° C.:0.1 N HCl, 0.1 N NaOH, saline, and rabbit plasma. The disappearance of the particles in the suspensions was noted by visual observations and the integrity of the particles was examined by scanning electron microscopy. To identify the degradation products, the residual solutions were subjected to analysis by HPLC. The HPLC system consisted of a RP-18 column, a Perkin-Elmer isocratic LC pump (Model 250), a PE Nelson 900 series interface, a Spectra-Physics UV/Vis detector (Model SP 8540) and a data station. The eluant (10% methanol in double distilled water) was run at 0.8 ml/min. with UV detection at 254 nm. Samples in HCl or NaOH were neutralized before injection. Plasma samples were first treated with PCA (0.4 N) and centrifuged to remove precipitate proteins. The supernatants were then injected for HPLC analysis.

Acute Toxicity $LD_{50}$ of IX-C particles was determined by injecting different volumes of particulate suspension (80 mg I/ml saline) into the tail veins of mice. Swiss Webster mice (Harlan Sprague Dawley Inc., Indianapolis, Ind.) weighing between 25 and 30 g were given doses ranging from 0.2 to 1 ml/mouse. Five animals were used for each dose. No anesthesia was used for injection. Following the injection, animals were monitored daily for 7 days. The percentage survival vs. dose curve was constructed to estimate $LD_{50}$.

Computed Tomography Studies in Normal Rabbits

New Zealand white rabbits (male, 3.0 to 3.5 kg) were anesthetized by an intramuscular injection of a solution containing xylazine (8.6 mg/ml), ketamine (42.9 mg/ml), and acepromazine (1.4 mg/ml) at a dose of 0.4 ml/kg for a long-lasting effect. Intravenous catheters (22-gauge) were placed in a marginal ear vein for the introduction of particle suspension. Rabbits were positioned supine in a GE model 9800 Quick scanner (Milwaukee, Wis.). The particulate contrast agent of proper volume (8% I, w/v in saline) was injected through the catheterized ear vein over a period of 10 to 15 minutes.

CT imaging of radiopaque particles (80 mg I/ml) was carried out at doses of 100, 200, and 270 mg I/kg body weight respectively. Three rabbits were used for each dose level. CT imaging was done with a scan speed of 1.0 seconds, 120 kV, 280 mAs, and a 25-cm field of view. Sequential, contiguous 3-mm-thick slices through the abdomen and 5-mm-thick-slices through the pelvis were obtained before contrast injection, immediately after injection and at various times (15 and 30 minutes, 1, 2, and 6 hours, and 1, 2, and 7 days after injection). The rabbits were killed with an overdose of pentobarbital sodium (50 mg/kg) administered via the catheterized ear vein.

Densitometric analysis of the liver, kidney, aorta, and bladder were performed. The density attenuation (HU) was obtained from 10 areas of interest from at least three slices. To minimize the partial volume effect, care was taken to ensure that no visible blood vessels were included in the area of interest. Organ enhancement vs. time curves for each dose administered were constructed to determine the pharmacokinetic profiles.

Computed Tomography Studies of Rabbit Liver Bearing VX2 Tumor

Four New Zealand white rabbits (3.0 to 3.5 kg) were inoculated at a single site in the liver with a 0.5 cc suspension of minced VX2 tumor fragments (~$10^6$ cells). The VX2 tumors were maintained through serial animal passage and were available from The University of Texas M.D. Anderson Cancer Center.

CT scans were performed 5 days after inoculation. After preinjection scanning, IX-C particles (80 mg I/ml) of dose 200 mg I/kg body weight were injected intravenously and abdominal scans were performed immediately after injection and at 15, 30, 60, and 120 minutes after injection. The animals were killed after scanning. The livers were cut transversely into slices of 2–3 mm to confirm the size and location of the hepatic tumors. The attenuation of tumor and the surrounding liver parenchyma were measured directly from CT scans.

Statistics

A P value less than 0.05 was considered to be significant. An unpaired two-tailed Student's t-test was used to compare liver attenuations between pre- and postcontrast groups.

RESULTS

IX-C Synthesis

The reaction scheme and the structure of the cyclic carbonate of IOXILAN obtained by reacting IOXILAN with CDI is shown in FIG. 1. The structure was confirmed by Infrared spectroscopy (IR), mass spectroscopy, and elemental analysis. Carbon-13 NMR indicated the presence of cyclic carbonate carbons. The spectrum was complicated by the existence of optical isomers conferred by the chiral carbons of the secondary alcohol and rotational isomers resulted from N-acetylated anilide nitrogens.

Particle Preparation and Characterization

IX-C particles could be easily prepared by a solvent extraction/evaporation process. Because IX-C has limited solubility in methylene chloride, a cosolvent (acetone) is necessary to facilitate IX-C solubilization. The presence of water-soluble acetone in the organic phase resulted in rapid phase separation because acetone was quickly extracted by the aqueous phase upon emulsification. When acetone was used alone, irregular particles were produced.

Figure 3:
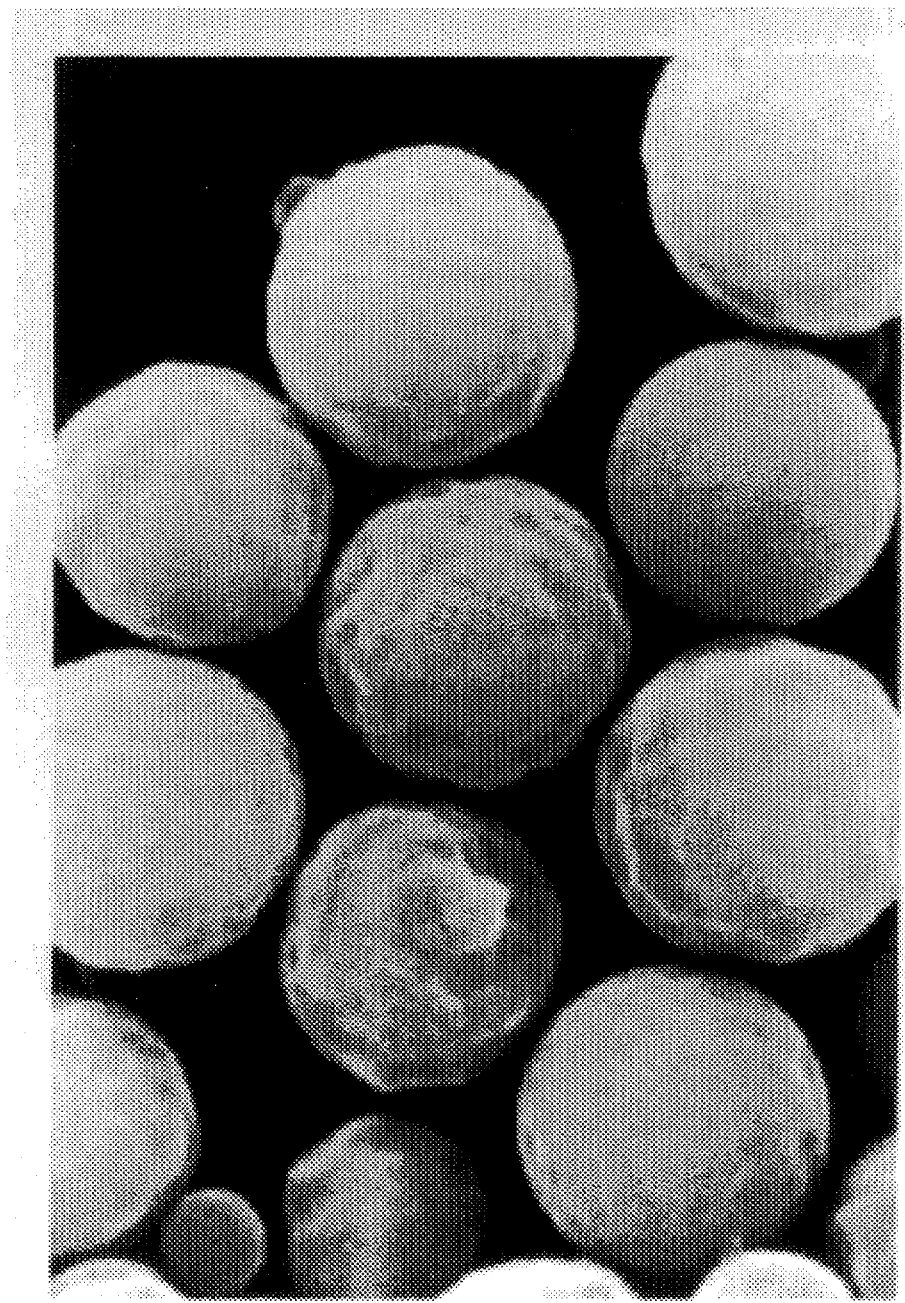
FIG. 3 is a scanning electron micrograph of the particles from FIG. 2.

IX-C particles thus prepared had an average diameter of 1.1 μm, with 95% of them ranging between 0.6 and 2.0 μm (number average) as determined by a submicron particle analyzer (FIG. 2). The iodine content of the particles was 45%. Scanning electron microscopy revealed that the particles were spherical in shape and had smooth surfaces (FIG. 3).

Suspension Stability

All IX-C particle formulations were stable. No particle aggregation was observed either in saline or in 0.1% Tween 80 solution. The IX-C particle suspensions were also stable when mixed with rat plasma (FIG. 4), indicating that the interactions between the IX-C particles and blood components (e.g., fibrinogen) were minimal.

Hydrolytic and Enzymatic Degradability

Figure 5:
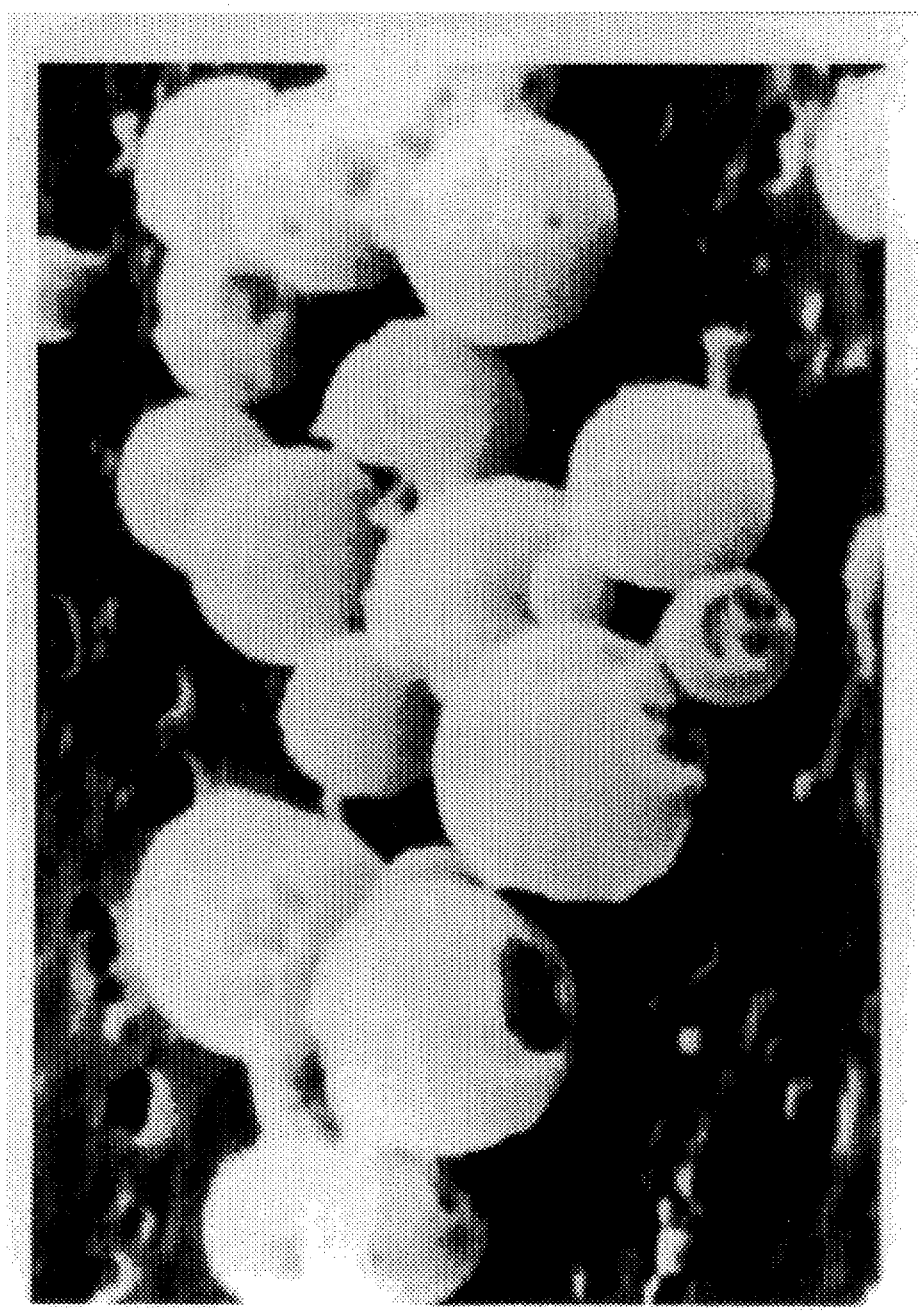
FIG. 5 is a scanning electron micrograph of the particles of FIG. 2 after incubation in saline at 37° C. for two weeks.

Cyclic carbonate of 1,2-diol has been prepared as a means to protect hydroxyl groups. It is stable in acidic condition, but is labile towards basic solution. To test their hydrolytic stability, IX-C particles were suspended in HCl, NaOH, saline, and plasma solutions at 37° C. As expected, when placed in NaOH solution, the IX-C particles were completely dissolved within 1 hour. The degradation of IX-C particles in both HCl and saline solutions was much slower. No gross changes in suspension appearance was observed during a 2-week period. However, the degradation did occur in both solutions as UV absorbance of the supernatants from the IX-C suspension increased steadily over the incubation period. As confirmed by scanning electron microscopy, IX-C started to crumble and disintegrate after being incubated in saline for 2 weeks (FIG. 5). In plasma suspension, where pH is slightly acidic, IX-C particles were completely dissolved in 6 days, indicating that an enzymatic effect played a significant role in the degradation of IX-C particles.

In order to determine the identity of IX-C degradation products, the supernatants of all samples were subjected to reverse-phase HPLC analysis. All samples had a distinct peak at 6.88 minutes. Standard IOXILAN had the same retention time under the same analytical conditions. Thus, it appeared that the degradation of IX-C yielded IOXILAN and carbon dioxide. To ascertain that the observed peak was not an artifact from plasma component, the plasma samples were also analyzed by FAB Mass spectroscopy. The presence of IOXILAN was confirmed by the molecular peak (MH+) of IOXILAN at 792.

Acute Toxicity

The $LD_{50}$ of IX-C particles determined with Swiss Webster mice was 1.4 g I/kg body weight for males and 1.2 g I/kg body weight for females. The doses correspond to 3.1 and 2.6 g/kg bodyweight IX-C respectively.

Computed Tomography

Figure 6:
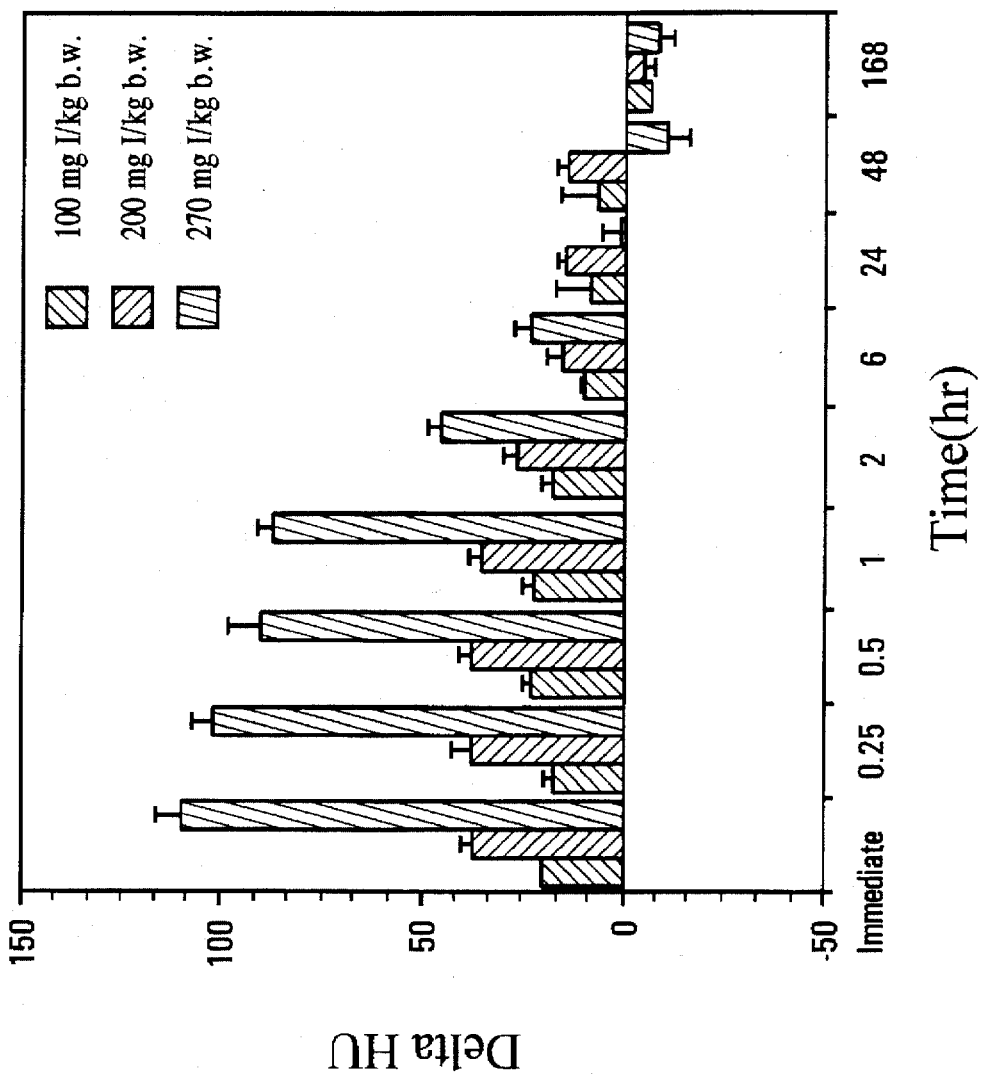
FIG. 6 is a plot of liver attenuation enhancement as a function of time for three doses of IX-C particles.

Liver attenuation enhancement (ΔHU) is plotted as a function of time for three doses of IX-C particles (FIG. 6). Significant attenuation enhancement of the liver was achieved over a period of 6 hours in a dose-dependent manner. Following intravenous administration of 100, 200, and 270 mg I/kg body weight of IX-C particles, maximum liver CT attenuation increases were 23, 38, and 110 respectively. Liver attenuation reached maximum at approximately 30 minutes postinjection. At 270 mg I/kg body weight, the attenuation enhancement was much greater compared with those of lower doses and reached maximum earlier. The attenuation enhancement persisted for 1 hour and started to decrease at 2 hours postinjection. Liver attenuation decreased to the preinjection value by 48 hours (FIG. 7). The increase in attenuation of the spleen was even more striking. Immediately after injection of 200 mg I/kg body weight of radiopaque particles, the Hounsfield units increased from a precontrast level of 20 to 265 HU. The attenuation of the spleen had reduced to 63 HU by 2 days postinjection. Gallbladder and bowel activity were observed at 6 hours postinjection (data not shown).

The CT pharmacokinetics of aorta, kidney (cortex and medulla), and bladder following the injection of 200 mg I/kg body weight of IX-C particles are presented as a histogram in FIG. 7. The attenuation of the aorta reached a maximum immediately after injection (ΔHU 43) and decreased rapidly to the preinjection level 1 hour after injection. IX-C or metabolites of IX-C could be visualized in the kidney immediately after injection. The kidney cortex attenuation reached maximum values of 94 HU at 2 hours postinjection, which was 50 HU higher than that of preinjection value. The kidney activity fell back to the preinjection level by 2 days (FIG. 7). For all doses studied, attenuation changes of the lungs were found to be negligible.

Computed Tomography of Rabbits Bearing VX2 Tumors

Figures 8A, 8B, 8C, 8D:
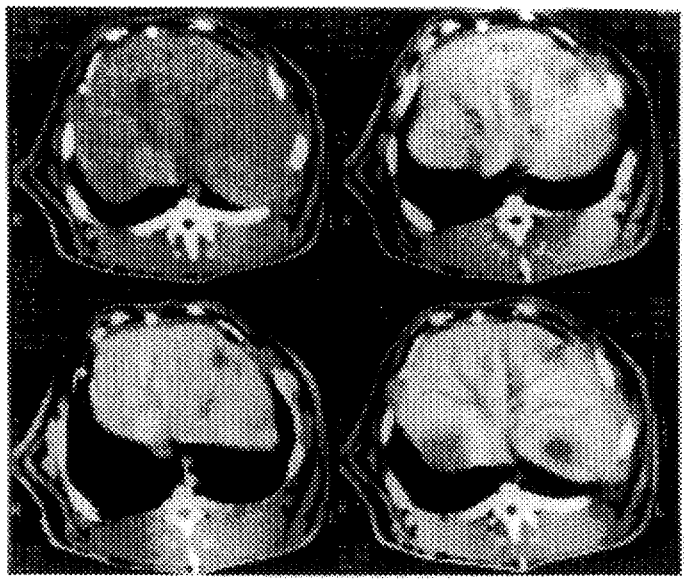
FIG. 8 represents CT imaging of a rabbit liver six days after tumor inoculation: "a" is the CT image before contrast injection; "b" after contrast injection; "c" and "d" after about 2 hours.

The CT imaging of a rabbit liver 6 days after tumor inoculation is shown in FIG. 8. The tumor was barely detectable at any level before contrast injection (FIG. 8a). Immediately after the injection of 200 mg I/kg body weight of IX-C particles, a tumor measuring 6-8 mm was clearly visible at the anterior-lateral portion of the right lobe (FIG. 8b). The visibility of the tumor persisted up to 2 hours (FIGS. 8c and 8d). The presence of the tumor was verified by necropsy in exactly the same location. For all four rabbits, the average increases in liver and tumor attenuation were 39 and 4 HU respectively at 30 minutes after injection. These values reflect an increase in the attenuation difference of 35 HU between the liver and the tumor.

DISCUSSION

The goal of the foregoing experiments is to develop a novel contrast agent that can be selectively delivered to the RES and improve the detectability of liver lesions on CT scans. The feasibility of using particulate CM as a hepatic macrophage imaging agent has been demonstrated. However, adverse reactions often have been associated with the administration of particulate CM, which has impeded its further development. One possible solution is to develop particulate CM that can be quickly degraded and cleared from the Kupffer cells and the liver. In this way, the impact of foreign particles on the function of the RES and the subsequent side reactions can be reduced to a minimum. Among the methods used to develop particulate CM, the prodrug approach has the advantage of being easier to prepare, less expensive, and having a higher iodine content on a weight basis. Since the degradation product is the original water-soluble CM, it is conceivable that radiopaque particles made of a non-ionic contrast agent would cause less osmotic toxicity than ionic CM.

Based on the above considerations, a new iodinated compound using IOXILAN as the substrate was designed. Treatment of IOXILAN with CDI in DMSO yielded cyclic carbonate and carbamate derivatives of IOXILAN, IX-C (FIG. 1). This compound is soluble in acetone, is slightly soluble in methylene chloride, and is insoluble in water. The lipid soluble property of the IX-C compound allowed the easy preparation of IX-C particles by a solvent extraction/evaporation procedure.

Because phagocytosis of foreign particles by the Kupffer cells generally results in Kupffer cell activation and disturbance in the microcirculation of the liver (Li et al., unpublished data), it is desirable that particulate CM designed for macrophage imaging will quickly be cleared from the liver after their functions are over. As shown in in vitro degradation studies, IX-C particles were extremely unstable in basic solutions. IX-C particle suspensions in saline at neutral pH underwent a slow, yet definite degradation. Of interest is the ability of IX-C particles to dissolve completely in rabbit plasma. This observation implies that various enzymes play a significant role in the dissolution of IX-C particles and will be an important factor in the in vivo fate of IX-C particles. The degradation of IX-C particles produced IOXILAN and carbon dioxide, both of which are not expected to impose a significant toxicity problem.

Figure 4:
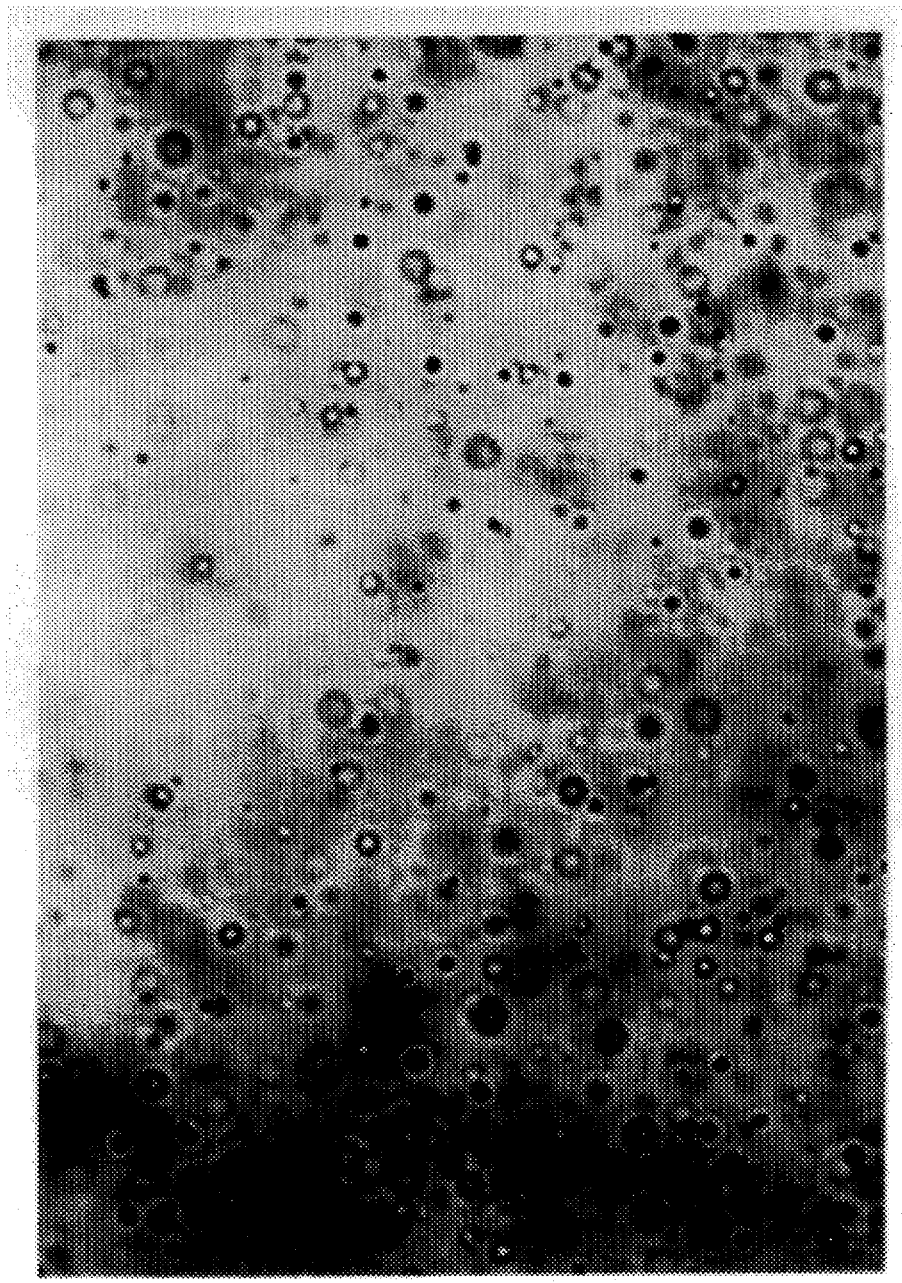
FIG. 4 illustrates the particles of FIG. 2 suspended in saline in the presence of rat plasma.

For the particles to be efficiently taken up by the RES and able to pass through capillaries without causing embolization, they must have proper shape, size, and size distribution. Furthermore, interactions of plasma components with small particles have to be minimized since they usually lead to particle aggregation. The suspension stability of IX-C in saline and other IX-C formulations was investigated. IX-C particles were stable in saline with no tendency to flocculate upon the addition of rat plasma (FIG. 4). Administration of IX-C suspension in saline at concentration as high as 8% I (w/v) did not cause lung embolization in rabbits, confirming the nonaggregation nature of IX-C particles.

The ability of IX-C particles to opacify the liver in rabbits was demonstrated in FIG. 6. The fact that the spleen was also highly opacified confirmed that the selective enhancement of the liver was due to macrophage uptake of the radiopaque particles. At a dose of only 100 mg I/kg body weight, IX-C particles enhanced attenuation to a satisfactory level ($\Delta HU > 20$). Moreover, the attenuation enhancement persisted for a period of 2 hours, allowing adequate time to conduct CT examination. Thus, radiopaque particles such as IX-C overcome one of the disadvantages of water-soluble CM, namely, fast distribution to the interstitial space.

Pharmacokinetic data were obtained by measuring changes in the attenuation of various organs in the rabbits. IX-C particles were rapidly cleared from the blood. Significant enhancement of gallbladder attenuation and enhanced bowel activity at 6 hours postinjection, indicating that IX-C particles were cleared via the hepatobiliary system. This observation is consistent with other particulate CM that also produced increased gallbladder opacity. The relatively short time (2 days) for the elimination of IX-C particles from the liver was clearly demonstrated. Thus, the degradability of IX-C particles was confirmed in vivo.

Surprisingly, IX-C particles were found to cause significant kidney attenuation enhancement immediately after contrast injection (FIG. 7). This observation may be attributed to the following. First, IX-C particles were quickly degraded to water-soluble products. The observed kidney activity was due to the excretion of the resulting water-soluble CM. Second, IX-C particles were caught in the tubule of the kidney. Although the exact cause of IX-C uptake in the kidney is not clear at present, metabolism and eventual excretion of IX-C particles by the kidney pathway was clearly demonstrated. The bladder CT attenuation at 6 hours after contrast injection was 240 HU higher than the precontrast level. HPLC analysis of urine samples taken at 2 hours and 6 hours postinjection revealed the presence of the degradation production IOXILAN. It was noted that the liver attenuation increased at a much faster pace when the injected dose reached a certain level (270 mg I/kg body weight) (FIG. 6). This observation can also be explained by the saturation of the kidney elimination pathway, which resulted in more particles being redirected to the liver. Therefore, unlike other previously reported radiopaque particles, IX-C particles were eliminated via both the hepatic and the urinary pathways.

Toxicity of particulate CM has been a major concern. The determined $LD_{50}$ of IX-C of 1.4 and 1.2 g I/kg body weight corresponded to 3.1 and 2.6 g of IX-C/kg body weight for male and female mice respectively. These values are slightly higher than those reported for other particulate CM. Since the suspension used in this study was very concentrated (800 mg I/ml), it is possible that the LD50 value would be higher if this suspension was diluted and injection was made in several portions (to reduce the volume effect). Using data from the CT imaging study, one can predict that the diagnostic dose for IX-C is 100 mg I/kg body weight. This would give a safety margin of more than ten-fold.

At a dose of 200 mg I/kg body weight, a tumor (6 mm in the smallest dimension) could be clearly detected in the postcontrast images (FIG. 8). The tumor was not visible in the precontrast image because it was either too small or isodense to liver parenchyma. Studies with rabbits bearing VX2 tumors demonstrated that IX-C particles could opacify the liver for about 2 hours without significant reduction of contrast enhancement, which allowed sufficient time for CT examinations.

The results showed that IX-C particles were biodegradable, with IOXILAN and carbon dioxide as the degradation products. The particles had an average size of 1-2 μm, and were stable in saline suspension. The $LD_{50}$ determined for IX-C particles was 2.6 and 3.1 g/kg body weight for females and males respectively. A dose of 200 mg I/kg body weight caused an increase of 38 HU in liver attenuation. In rabbit, hepatic clearance of the contrast medium in 2 days was demonstrated. A tumor barely visible in precontrast scans could be detected after contrast injection.

CONCLUSION

Biodegradable IX-C particles have suitable physico-chemical characteristics as a particulate CT contrast agent, and are effective as a macrophage imaging agent.

The foregoing invention was explained with reference to a particular embodiment. One skilled in the art will recognize that many modifications may be made to the present invention without departing from the spirit and scope of the invention. The embodiment described herein is meant to be illustrative only and should not be taken as limiting the invention, which is defined in the following claims.

We claim:

1. A method for producing a precursor for a radiopaque particulate contrast agent for selectively detecting lesions in the liver and spleen, said contrast agent being biodegradable into non-ionic by-products, said method comprising the steps of:

providing a non-ionic, water soluble, radiopaque contrast agent comprising an aromatic ring bonded to at least one radiopaque substituent and to at least one amide group at the carbon or the nitrogen of the amide moiety, said amide group having a substituent selected from the group consisting of an aliphatic 1,3-diol and a vicinal diol;

thoroughly mixing said contrast agent with an activating agent and a polar aprotic solvent in the presence of a catalyst;

reacting said mixture for a time and at a temperature sufficient to form said precursor by changing said diol substituent on said amide into a compound selected from the group consisting of a cyclic carbonate, a carbamate, and mixtures thereof; and separating said precursor from said polar aprotic solvent.

2. The method of claim 1 further comprising the step of isolating a purified form of said precursor.

3. The method of claim 1 further comprising the steps of mixing said precursor with an organic solvent; emulsifying said mixture; and removing said organic solvent to form said particulate contrast agent.

4. The method of claim 2 further comprising the steps of mixing said precursor with an organic solvent; emulsifying said mixture; and removing said organic solvent to form said particulate contrast agent.

5. The method of claim 1 wherein said catalyst is a salt of an alkyl oxide.

6. The method of claim 3 wherein said catalyst is a salt of an alkyl oxide.

7. The method of claim 3 wherein said organic solvent comprises acetone and methylene chloride.

8. The method of claim 4 wherein said organic solvent comprises acetone and methylene chloride.

9. The method of claim 3 wherein said emulsifying step comprises adding an emulsifier selected from the group consisting of polyvinyl alcohol, TWEEN 80, cellulose, and polyvinylpyrrolidone.

10. The method of claim 4 wherein said emulsifier comprises polyvinyl alcohol.

11. The method of claim 1 wherein said radiopaque particulate contrast agent has the following structure: wherein R comprises a radiopaque element;

$R_1$ is an amide group bonded to said aromatic ring at either the nitrogen or the carbon of the amide, the unbonded nitrogen or carbon having a substituent selected from the group consisting of an aliphatic vicinal diol and an aliphatic 1,3-diol; and $R_2$ is selected from the group consisting of a radiopaque element, a hydrogen, an alkyl group having between about 1-4 carbon atoms, and an amide group bonded to an aromatic carbon at either the nitrogen or the carbon of the amide moiety, the unbonded nitrogen or carbon of said amide moeity having a substituent selected from the group consisting of hydrogen, an alkyl group having between about 1-3 carbon atoms, and a hydroxylated aliphatic side chain having between about 1-8 carbon atoms.

12. The method of claim 11 wherein said radiopaque substituents comprise iodine.

13. The method of claim 12 wherein at least two of said R groups comprise iodine and at least one of said $R_2$ groups comprises said amide group having a substituent selected from the group consisting of an aliphatic vicinal diol and an aliphatic 1,3-diol.

14. The method of claim 1 wherein said water-soluble non-ionic contrast agent is selected from the group consisting of IOHEXOL, IOPROMIDE, IOTROLAN, IOPAMIDOL, METRIZAMIDE, IOGLUNIDE, IOGULAMIDE, and combinations thereof.

15. The method of claim 3 wherein said water-soluble non-ionic contrast agent is selected from the group consisting of IOHEXOL, IOPROMIDE, IOTROLAN, IOPAMIDOL, METRIZAMIDE, IOGLUNIDE, IOGULAMIDE, and combinations thereof.

16. The method of claim 4 wherein said water-soluble non-ionic contrast agent is selected from the group consisting of IOHEXOL, IOPROMIDE, IOTROLAN, IOPAMIDOL, METRIZAMIDE, IOGLUNIDE, IOGULAMIDE, and combinations thereof.

* * * * *